Figure 1:
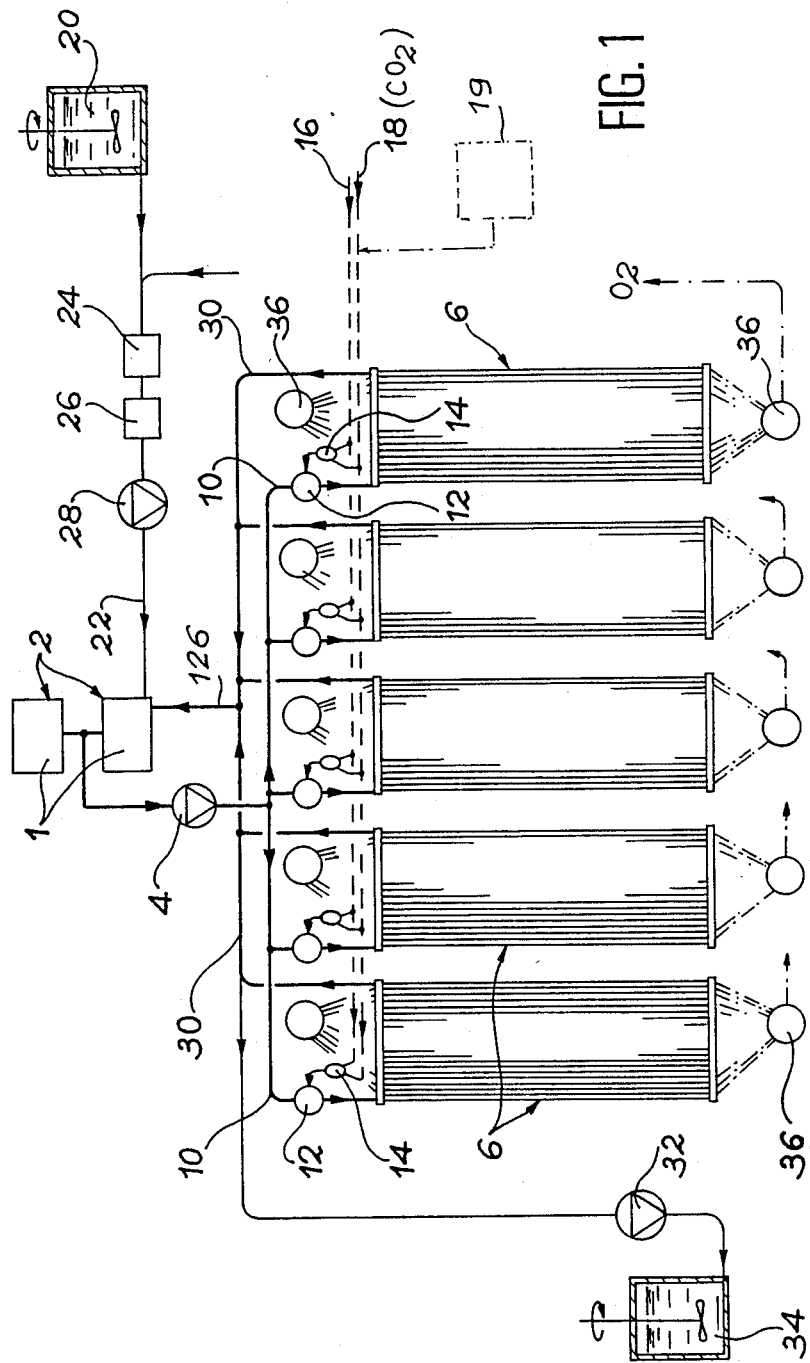

United States Patent [19]

Berson et al.

[11] Patent Number: 4,868,123
[45] Date of Patent: Sep. 19, 1989

[54] APPARATUS FOR THE INTENSIVE, CONTROLLED PRODUCTION OF MICROORGANISMS BY PHOTOSYNTHESIS

[75] Inventors: Xavier Berson, Jouques; Michel Bouyssou, Vinon sur Verdon; Yves Castel, Les Milles; Daniel Chaumont, Venelles; Claude Gudin, Aix en Provence, all of France

[73] Assignee: Commissariat a l'Energie Atomique, Paris, France

[21] Appl. No.: 252,186

[22] Filed: Sep. 30, 1988

[30] Foreign Application Priority Data

Oct. 2, 1987 [FR] France ............................. 87 13647

[51] Int. Cl.⁴ .............................................. C12M 1/38
[52] U.S. Cl. ...................................... 435/290; 435/301; 210/149; 210/180; 210/181; 210/242.1
[58] Field of Search ....................... 435/290, 301, 313; 126/415; 210/149, 180, 181, 242.1

[56] References Cited

U.S. PATENT DOCUMENTS 2,732,663  1/1956  Dewey .
3,933,628  1/1976  Varani .................. 126/415

FOREIGN PATENT DOCUMENTS 2324224  4/1977  France .
2361060  3/1978  France .

Primary Examiner—Carroll B. Dority, Jr.
Attorney, Agent, or Firm—Pearne, Gordon, McCoy & Granger

[57] ABSTRACT

Apparatus for the intensive, controlled production of microorganisms by photosynthesis.

This apparatus comprises at least one photobioreactor (6) to be placed on an expanse of water (8), which has first group of flexible tubes (38), which are transparent to light and in which circulates the culture medium and a second group of inflatable tubes (62), disposed and maintained beneath the first group by means of detachable Y-shaped interpolated members (70), which are regularly spaced. At least one two-column carbonator (12) connected to the photobioreactor intake (43) for charging the liquid medium with the $CO_2$ necessary for photosynthesis is provided. Two degassing means (36) connected to the two ends of the photobioreactor are provided for eliminating the oxygen produced by the microorganisms from the liquid medium. There is at least one expansion tank (2) connected to the photobioreactor (6) for reducing possible volume variations in the photobioreactor (6).

15 Claims, 8 Drawing Sheets

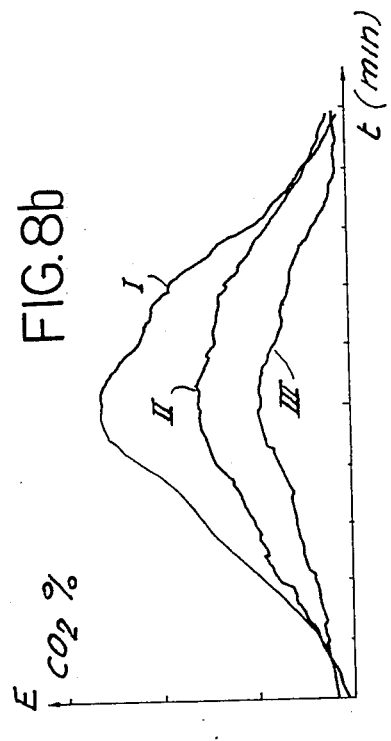
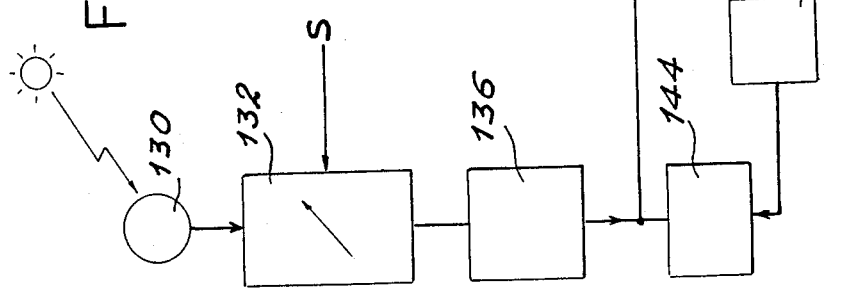
FIG.8b
FIG.8a

APPARATUS FOR THE INTENSIVE, CONTROLLED PRODUCTION OF MICROORGANISMS BY PHOTOSYNTHESIS

DESCRIPTION

The present invention relates to an apparatus for the intensive, controlled production of microorganisms or biomass, by photosynthesis and on an industrial scale, using simple components and which has a simple construction.

The invention is applicable to the production of any photosynthetic material, i.e. any life form liable to development and photosynthesis in an appropriate nutrient liquid medium in the presence of solar radiation and carbon dioxide, to the production of metabolites and polysaccharides possibly excreted by microorganisms. Examples of photosynthetic microorganisms are vegetable tissues and monocellular organisms containing chloroplasts, photosynthetic bacteria and microalgae.

Photosynthesis is the transformation, as a result of solar energy, of carbon dioxide into primary hydrocarbon material, oxygen being the main by-product of said biochemical transformation. The latter can be symbolized by the following Myers equation:

$$6.14\ CO_2 + 3.65\ H_2O + NH_3 \rightarrow C_{6.14}H_{10.3}O_{2.24}N + 6.85\ O_2$$

Nitrogen is supplied in the form of nitrate, urea of ammonium salts introduced into the liquid medium containing the microorganisms.

The culture and development of the microorganisms by photosynthesis is carried out in a photobioreactor. In order to ensure a good operation of the latter and an optimum development of the microorganisms, it is necessary for a certain number of physical phenomena to be controlled.

In particular, the liquid medium containing the microorganisms must be constantly charged with dissolved $CO_2$ and nitrogen, the nitrogen and dissolved $CO_2$ concentration being maintained at an optimum level throughout the culture and the development of the microorganisms. In the same way, the temperature of the liquid medium containing the microorganisms, its salinity, its concentration of photosynthetic cells, as well as its pH must be very carefully regulated.

The presently known photobioreactors are constituted by an assembly of transparent tubes placed in the form of a raft above a large expanse of water (lagoon, pond, pool, ocean) serving as cooling sources for the microorganism-charged liquid medium circulating in the tubes.

Examples of tubular photobioreactors are given in FR-A-2 324 224 and 2 361 060.

In order to obtain a good heat regulation of the culture medium, it is necessary to eliminate any gas within the photobioreactor tubes, the static, constant presence of any gas and in particular the oxygen resulting from the photosynthesis being prejudicial to the operation of the photobioreactor. Thus, it is necessary to continuously extract the gases and in particular the oxygen present in the tubes.

As the cooling of the culture medium is ensured by immersing all or part of the tubular photobioreactor in the underlying water, the presence of gas pockets within these tubes makes it difficult or impossible to immerse the same leading to a considerable increase in the temperature of said tubes caused by solar radiation.

This more particularly leads to a drying out of the micro-organisms on the inner wall of the uncooled tubes. The thus formed solid microorganism film makes it impossible for there to be any diffusion of sunlight, so that there is a less satisfactory utilization of solar energy and consequently the photobioreactor has a poor efficiency. Moreover, presence of oxygen in the tubes can be prejudicial or even toxic for the microorganism cultured in the tubes.

In is therefore necessary to design an apparatus for the production of microorganisms by photosynthesis preventing any presence of air and in particular oxygen within the tubes containing the microorganisms-charged liquid medium.

In order to prevent inter alia the formation of gas pockets in the tubes of a photobioreactor, plastic balls are introduced into the tubes containing the culture medium. These balls, which are circulated with the culture medium, ensure an agitation and cleaning of the tubes by friction on the walls of the latter. Such a system for the cleaning and degassing of the tubes of a photobioreactor is described in FR-A-2 576 034.

Although such a system of self-cleaning and degassing walls is suitable for a photobioreactor located on a rigid, planar surface, it cannot be used when such a photobioreactor floats on an expanse of water. In addition, this self-cleaning walls system does not ensure a 100% effective degassing of the photobioreactor culture tubes.

Therefore the invention relates to an apparatus for the production of microorganisms by photosynthesis having one or more tubular photobioreactors to be placed on an expanse of water, preventing any gaseous pockets and in particular oxygen within the said tubes.

The invention therefore specifically relates to an apparatus for the intensive, control production by photosynthesis of microorganism suspended in a liquid medium:

at least one photobioreactor to be placed on an expanse of water and having a first group of tubes, which are transparent to light and in which circulates the liquid medium, and a second group of tubes disposed and maintained beneath the first group of tubes by means of regularly spaced, detachable interpolated members, said second group being able to make the photobioreactor submersible or non-submersible, means for controlling the second group of tubes with a view to the immersion or non-immersion of the photobioreactor, at least one carbonator connected to the inlet of the photobioreactor in order to charge the liquid medium with the $CO_2$ necessary for photosynthesis, at least one degassing means connected to the photobioreactor for eliminating from the liquid medium the oxygen produced by the microorganisms and possibly the undissolved $CO_2$ and at least one expansion tank connected to the photobioreactor in order to reduce possible variations in the volume within the photobioreactor.

Advantageously, the tubes of the first group are interconnected so as to form a coil. In the same way, the tubes of the second group are interconnected so as to form another coil.

The presence of the interpolated member makes it possible to render perfectly integral the two groups of tubes of the photobioreactor and in particular prevent the misalignment of the tubes, thus permitting by a linear entrainment of the liquid medium up to the degassing means, the circulation of gaseous pockets possibly present in the tubes of the first group, such as oxygen resulting from the photosynthesis. If balls are possibly used for cleaning the inner wall of the tubes of the first group, the presence of the interpolated members aids the circulation of these balls.

The interpolated members can be easily fitted and make it possible to prevent the tubes sticking or welding to one another, which prevents the changing of a single tube in the case of deterioration thereof.

According to the invention, when the temperature of the microorganism-charged liquid exceeds an upper reference temperature the photobioreactor is immersed through the deflation of the tubes of the second group, said deflation being ensured with the aid of an automaton. Conversely, when the temperature of the liquid medium is below the minimum reference temperature, the automaton controls the inflation of the tubes of the second group with compressed air.

The immersion of the photobioreactor can also be ensured by introducing a relatively heavy liquid into the tubes of the second group, whilst floating can be ensured by injecting a light fluid other than air.

The presence of interpolated members according to the present invention also improves the heat regulation of the photobioreactor, particularly when tubes of the second group are intended to be inflated with compressed air, so as to float the photobioreactor, as well as deflated with a view to the total or partial immersion of the photobioreactor.

Thus, in the absence of the interpolated members, during the immersion of the photobioreactor, with a view to cooling the microorganism-charged liquid medium, the tubes of the first group filled with liquid, heavier than the tubes of the second air-free group, might slide between two inflattable tubes and consequently remain constantly and totally immersed.

In order to improve the degassing of the photobioreactor and in particular in order to eliminate the oxygen produced, by photosynthesis, by the microorganisms, use is made of a degassing means of a particular design. This degassing means can be used with a tubular photobioreactor equipped with interpolated members according to the invention, or with tubular photobioreactors according to the prior art not having interpolated members.

For this purpose, the invention also relates to an apparatus for the intense, controlled production, by photosynthesis, of microorganisms suspended in a liquid medium comprising:

at least one photobioreactor to be placed on an expanse of water and having a first group of tubes, which are transparent to light and in which circulates the liquid medium and a second group of tubes, positioned beneath the first group, said second group being able to render the photobioreactor submersible or non-submersible, at least one carbonator connected to the inlet of the photobioreactor for charging the liquid medium with the $CO_2$ necessary for photosynthesis, at least one degassing means connected to the photobioreactor for eliminating from the liquid medium in particular the oxygen produced by the microorganisms, said degassing means having a sealed external enclosure with a longitudinal axis, a U-shaped duct for collecting oxygen, whereof one of the branches is located in the enclosure parallel to said axis and whose base is located on the side of the base of the enclosure, the end of said duct collecting the oxygen issuing into the upper part of the enclosure, at least one supply pipe and at least one discharge pipe for the liquid medium issuing into the lower part of the enclosure and at least one expansion tank connected to the photobioreactor for reducing possible variations in the volume in said photobioreactor.

The use of a degassing means according to the invention prevents the internal dirtying of the tubes of the photobioreactor (by the deposition of microorganisms), thus making it unnecessary to use the self-cleaning balls according to FR-A-2 576 034.

As has been stated hereinbefore, any static, constant presence of a gas of any type within the tubes of the first group is prejudicial to the use of the photobioreactor. This not only applies to the oxygen produced by the microorganisms, but also to the carbon dioxide introduced into the liquid medium and which is necessary for development of the microorganisms and for the air possibly used as a support gas for the carbon dioxide gas.

It is also important to use a carbonator ensuring an effective dissolving of the carbon dioxide injected into the microorganism-charged liquid medium. The carbonator according to the invention can be used with a tubular photobioreactor either equipped or not equipped with interpolated members, associated with a degassing means according to the prior art or according to the invention.

For this purpose, the invention also relates to an apparatus for the intense, controlled production, by photosynthesis, of microorganisms suspended in a liquid medium comprising:

at least one photobioreactor placed on an expanse of water and having a first group of light-transparent tubes, in which circulates the liquid medium, as well as a second group of tubes, located beneath the first group, said second group being able to make the photobioreactor submersible or non-submersible, means for controlling the second group of tubes with a view to the immersion or non-immersion of the photobioreactor, at least one carbonator connected to the inlet of the photobioreactor for charging the liquid medium with the $CO_2$ necessary for photosynthesis, said carbonator being of the type having two columns with an intake column in which the liquid medium is charged with $CO_2$ and a discharge column, connected to the intake column, in which is introduced the $CO_2$-charged liquid medium, at least one degassing means connected to the photobioreactor for eliminating from the liquid medium the oxygen produced by the microorganisms and at least one expansion tank connected to the photobioreactor for reducing possible variations of the volume in the photobioreactor.

The function of the first column is to bring about a maximum charging of the culture medium with carbon dioxide, whilst the function of the second column is to prevent the entrainment of carbon dioxide into the photobioreactor which has not dissolved in the liquid medium and possibly the air used as a support gas for $CO_2$.

In order to assist the $CO_2$ enrichment of the liquid medium, the intake column advantageoulsy has a plunger tube for supplying $CO_2$ into the liquid medium and whose plunging end is made from variable porosity, fritted stainless steel or glass. In addition, the first column can have an internal lining.

The expansion tank or tanks must, according to the invention, be shaped such that there is no accummulation of organic matter and in particular microorganisms, all the microorganisms generally being recycled. In addition, these tanks must be transparent to light.

Advantageously the expansion tank or tanks are transparent and formed by an enclosure with rounded edges, whose upper end is sealed by a diamond point cover and whose lower end is funnel-shaped.

The shape and transparency of these tanks constitute two means for combatting the accummulation of biomass, where anaerobic fermentation takes place and consequently prevents dead zones and contamination by certain light-sensitive protists (microorganisms).

Moreover, in certain cases, the shape of the tanks may make it possible to carry out a clarification of the culture during certain contaminations, i.e. filling of the tank with the culture, stopping circulation and sedimentation. The supernatant part containing the contaminants (such as 5 to 10 u microalgae) is eliminated and replaced by fresh culture medium. The sedimented parts (representing cultured microalgae) is recycled.

Other features and advantages of the invention can be gathered from the following non-limitative, illustrative description relative to the drawings, wherein show:

FIG. 1 an overall diagram of a microorganism production apparatus according to the invention and operating in a continuous manner.

Figure 2:
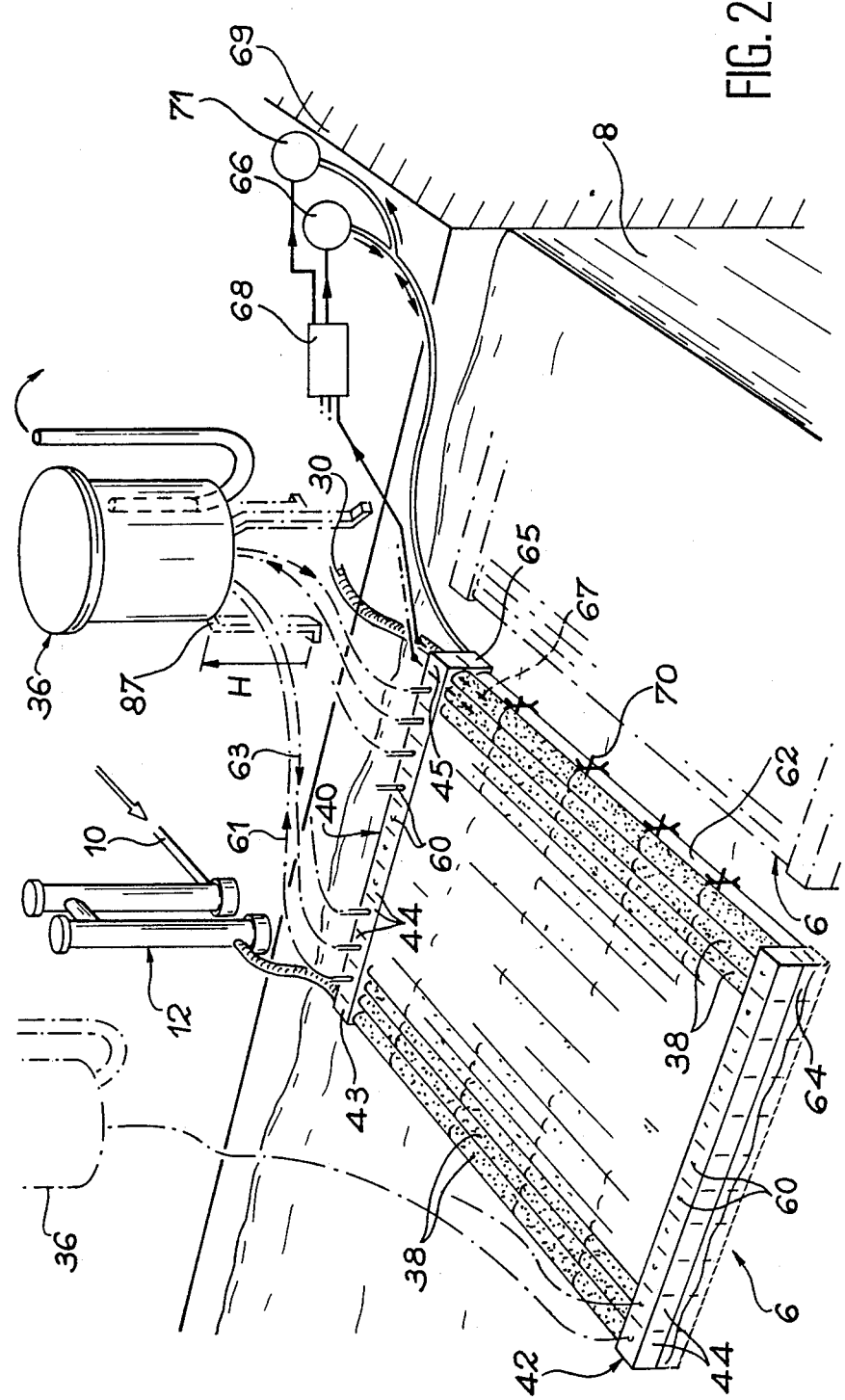

FIG. 2 in greater detail certain elements of the apparatus of FIG. 1.

Figure 3:
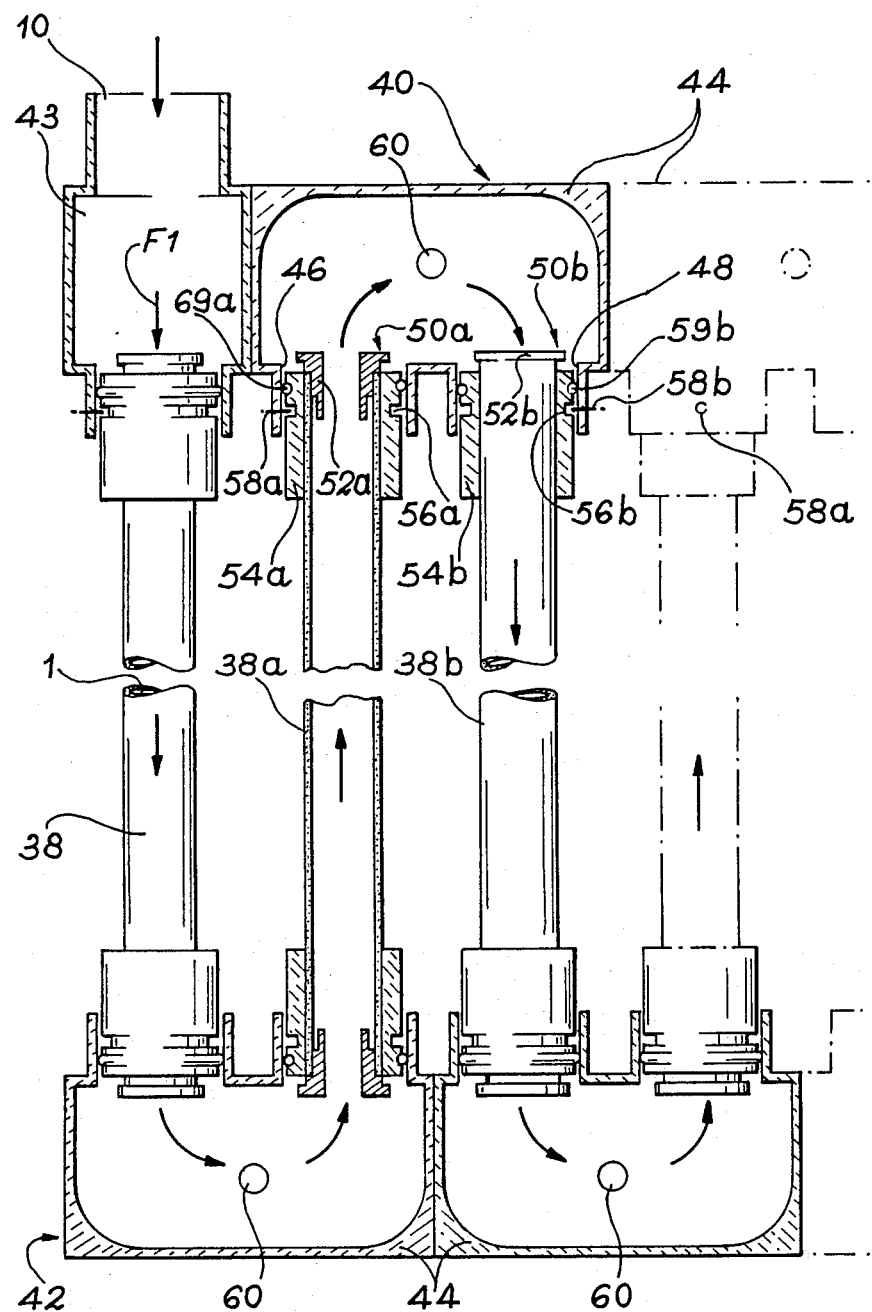

FIG. 3 diagrammatically and in longitudinal section, the photobioreactor tubes in which circulates the culture medium and which are interconnected, according to the invention.

Figure 4:
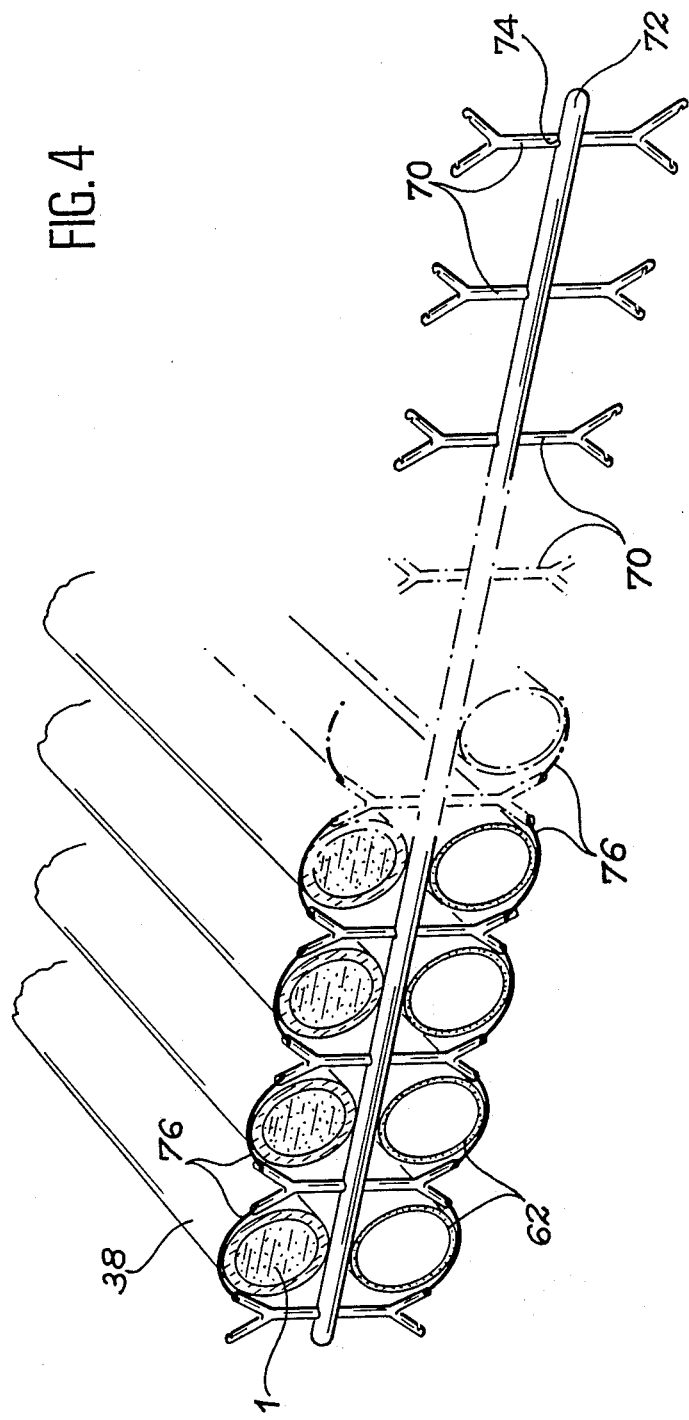

FIG. 4 in perspective, the two groups of tubes held together with the aid of interpolated members according to the invention.

Figure 5:
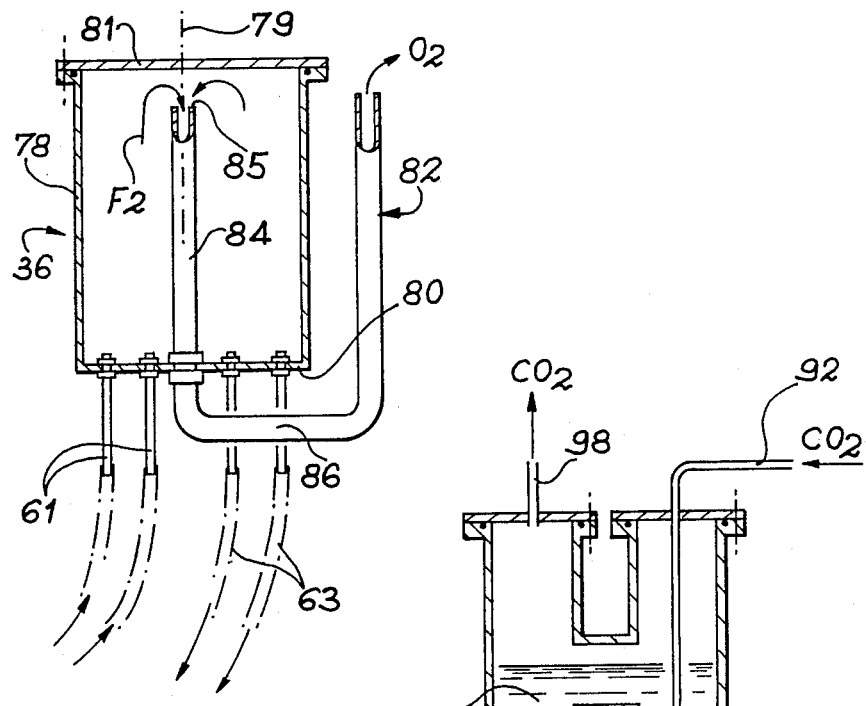

FIG. 5 diagrammatically and in longitudinal section, a degassing means according to the invention.

Figure 6:
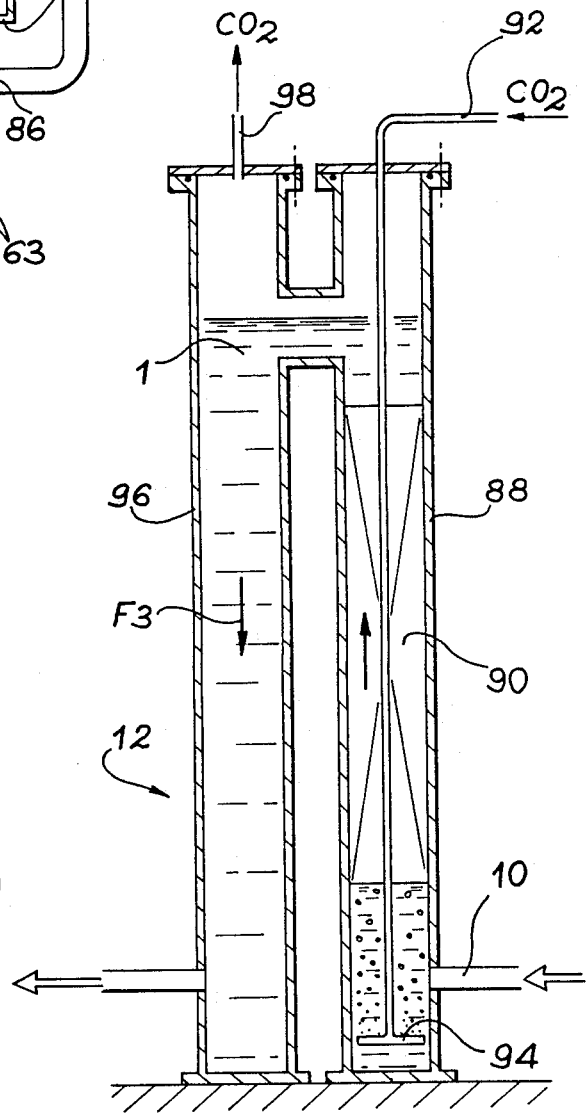

FIG. 6 diagrammatically and in longitudinal section, a carbonator according to the invention.

Figure 7:
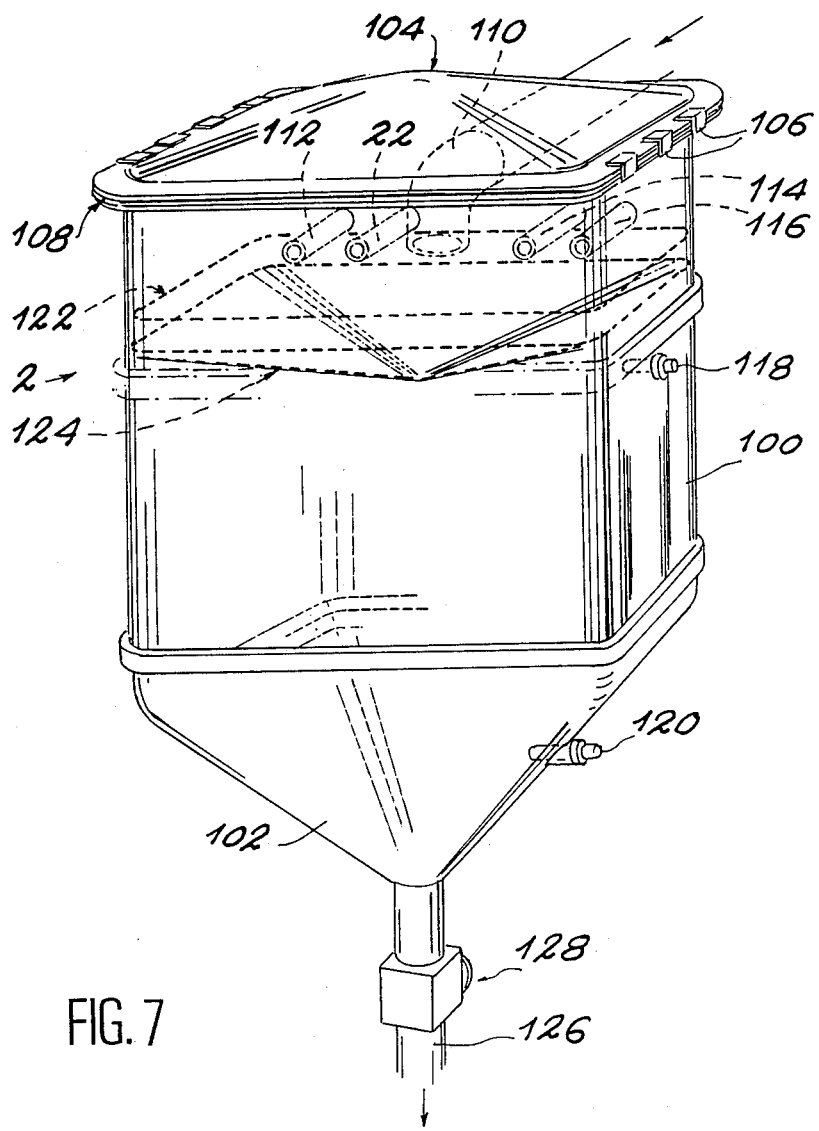

FIG. 7 diagrammatically and in perspective, an expansion tank according to the invention.

FIG. 8a is a schematic illustration of the regulation system of the invention. FIG. 8b shows graphs of solar energy, $CO_2$ supply and unconsumel $CO_2$ variations.

With reference to FIGS. 1 and 2, the apparatus for producing microorganisms by photosynthesis according to the invention comprises one or more approximately 200 1 expansion tanks 2 for receiving a solution of microalgae 1, injected with the aid of a pump 4 into tubular photobioreactor 6. The latter are to be placed on the surface of an expanse of water 8. The number of such photobioreactors is a function of the envisaged biomass production. Tanks 2 serve to reduce possible variations in the volume within the photobioreactors due to possible gas accumulation. The culture from all the photobioreactors passes into the tanks. In addition, the latter constitute a volume representative of the entire culture medium 1 of the apparatus in production. It is at this level where the supply of microalgae and culture medium takes place, as will be subsequently shown relative to FIG. 7.

The pipes 10 for the supply of culture medium to the photobioreactors are in each case equipped with twin column carbonators 12 in order to charge the culture medium 1 with the carbon dioxide necessary for photosynthesis. The number of carbonators 12 is generally the same as the number of photobioreactors.

The $CO_2$ supply takes place mixed with air, with up to 80% by volume of $CO_2$ in the mixture. For this purpose, a mixerflowmeter 14, mounted on the air supply pipe 16 and on the $CO_2$ supply pipe 18 is provided at the inlet for the gases into each carbonator 12. A system 19 makes it possible to regulate the $CO_2$ quantity introduced into the photobioreactors as a function of solar energy.

This production apparatus also comprises a tank 20 used for the preparation, accompanied by stirring, of the nutrient medium necessary for the growth of he microorganisms. This nutrient medium, prior to introduction via a supply pipe 22 into the tanks 2 containing the microalgae, is filtered by means of two Philippe-type filters 24,26, respectively ensuring the passage of the mineral and organic elements necessary for the growth of microorganisms, of 40 and 1 $\mu$m. The nutrient medium is injected into tanks 2 by a pump 28.

The microorganisms produced in the photobioreactor 6 are extracted at the outlet of each of these photobioreactors, via discharge pipes 30, with the aid of a volumetric pump 32. The feed of culture medium 1 of extraction pump 32 is equal to that of the nutrient medium injection pump 28, so that the culture volume in the photobioreactor remains constant. The microorganisms produced are recovered in a tank 34, under continuous agitation.

In order to ensure the degassing of the tubes of the photobioreactors and in particular to eliminate the oxygen produced, by photosynthesis, in the photobioreactor 6, degassing means 36 are provided on either side of the photobioreactor 6 (i.e. two degassing means per photobioreactor).

According to the invention, the photobioreactors are constituted by a first group of parallel tubes 38 made from a transparent, flexible plastic material, such as polyethylene. These tubes receive the culture medium 1 charged with nutrient elements and $CO_2$ necessary for the growth of the microorganisms. They have an approximate length of 15.8 m and an internal diameter of 63 mm. Tubes 38 are interconnected at their two ends, as shown in FIG. 3, with the aid of two collectors, respectively upstream 40 and downstream 42.

These collectors 40,42 are made from polypropalene and have several compartments or bent connections 44. The total number of compartments 44 of the upstream and downstream collectors is equal to the number of tubes 38.

Each compartment or connection 44 of the upstream collector 40 comprises an intake port 46 for receiving a first tube 38a and a discharge port 48 for receiving a second tube 38b. The fixing of tubes 38a and 38b to collector 40 is ensured with the aid of identical stuffing box systems respectively 50a and 50b.

For this purpose, two internal sleeves 52a, 52b are respectively located in tubes 38a and 38b and two external tubes 54a, 54b into which are fitted tubes 38a and 38b respectively are respectively located in the intake port 46 and discharge port 48 of compartments 44. Each of the external sleeves 54a, 54b is provided with a groove 56a, 56b, in which are placed screws 58a, 58b mounted on connection 44, respectively at the inlet and outlet of the latter.

Elastomer O-rings respectively 59a and 59b located on the outer face of the external sleeves 54a, 54b ensure the sealing of the assembly.

According to the invention, the internal sleeves 52a, 52b and the external sleeves 54a, 54b are made from polypropalene.

The assembly of the downstream collector 42 and tubes 38 is identical to that of the upstream collector 40 and tubes 38.

Within the thus formed coil circulates the culture medium 1 charged with $CO_2$ and nutrient elements, as indicated by arrows F1.

Each photobioreactor 6 has a single culture medium supply pipe 10, mounted at the inlet 43 of the upstream collector 40 and a single discharge pipe 30 for said medium, fitted to the outlet 45 of collector 40, the intake pipe 10 being fitted on the first photobioreactor tube 38 and the discharge pipe 30 on the final photobioreactor tube 38.

According to the invention, each connection 44 of the upstream and down stream collectors 40,42 respectively is provided with an orifice 60 for the connection of degassing means 36. This connection is ensured with the aid of flexible pipes for the supply 61 and the discharge 63 of the culture medium (FIGS. 2 and 5).

The temperature of the solution of the microorganisms must be regulated to between 10° to 28° C. for its own growth, i.e. close to ambient temperature. For this purpose, each photobioreactor 6 is provided with a second group of tubes 62 placed beneath tubes 38. These tubes 62, which are made from a flexible plastics material, e.g. polyethylene, are interconnected in the same way as tubes 38 with the aid of an upstream collector 64 and a downstream collector 65, having bent compartments, so as to form a coil (FIG. 2). These tubes 62, which are 16.4 m long and have an internal diameter of 63 mm are to be inflated with compressed air with the aid of an electrovalve 66, thus forming a pneumatic support floating on the surface of the expanse of water 8.

Electrovalve 66 is controlled by an electronic control circuit 68 connected to temperature measurement probes or sensors 68 located within tubes 38.

When the temperature of the culture medium 1 contained in tubes 38 and measured by probes 67 is above a maximum reference temperature (e.g. 29° C.), the temperature probes emit a first signal detected by the electronic circuit 68, which then controls the deflation of the tubes 62 via electrovalves 71. The deflation of tubes 62 then leads to the total or partial immersion as a function of the deflation level, of the photobioreactor 6 in the expanse of water 8. As the water is colder than the ambient atmosphere and the culture medium present in the photobioreactor, the culture medium cools.

When the immersed culture medium reaches a temperature, measured by probes 67 which is below a minimum reference temperature (e.g. 17° C.), the probes 67 emit a second signal detected by the electronic circuit 68 controlling electrovalve 66, so as to ensure the inflation with compressed air of tubes 62. The inflation of tubes 62 then leads to the floating of photobioreactor 6. The culture medium then reheats in the open air.

All the supply and discharge pipes for the culture medium, compressed air, etc. and all the electrical connections (probes 67), connected between the photobioreactors and the other components of the production apparatus, such as degassing means, carbonators, compressors, etc. are necessarily flexible in order to be compatible with the immersion or non-immersion of the photobioreactors. The components, other than the photobioreactors, are mounted on a hard pontoon 69, as shown in FIG. 2, floating on the water surface 8.

According to the invention, interpolated members 70, shown in FIGS. 2 and 4, maintain tubes 38 and 62 in place. These interpolated members 70 are detachable and regularly spaced roughly every 60 cm (FIG. 2). These interpolated members 70 are made from polypropylene and are shaped like a Y, whose tails are supported by support rods 72, made more particularly from polypropylene. To this end, supports 72 are equipped with orifices 74 in which are located the tails of the Y 70. The Y's located on either side of the rods 72 and respectively serving to maintain in place tubes 38 and 62, are fixed head to tail.

The Y's 70 are interconnected with the aid of flexible rubber connections mounted on the branches of the Y's. Tubes 38 and 62 are placed between two consecutive Y's 70, their maintaining in place being ensured by elastic connections 76 and support 72.

The heat regulation described hereinbefore, as well as the satisfactory operation of the photobioreactor 6 imply the total absence of gas within the photobioreactor tubes 38. For this purpose, use is made of degassing means 36, advantageously produced in the manner shown in FIG. 5 and connected to each end of the tubes 38.

Each degassing means 38 has a cylindrical external enclosure 78 with a longitudinal axis 79, provided with a base 80 and closed by a cover 81, as well as a U-shaped duct 82 for collecting oxygen and the other gases present in the culture medium 1. This U-shaped duct 82 has a branch 84 located along the longitudinal axis 79 of enclosure 78. The end 85 of branch 84 collects oxygen coming from the culture medium and issues into the upper part of enclosure 78 in the vicinity of cover 81. The base 86 of the U-shaped duct is parallel to the base 80 of enclosure 78. The oxygen flow direction in degassing means 36 is indicated by arrows F2.

The flexible supply pipes 61 for the oxygen-charged culture medium (generally 60% by volume of oxygen) and the flexible discharge pipes 63 for the deoxygenated culture medium and which are generally degassed issue at the base of the degassing means and are fixed to the base 80 of enclosure 78.

As indicated in FIG. 2, the degassing means 36 are supported by feet 87, whose height H is regulated in such a way that the enclosure 78 of the degassing means is never filled with culture medium, no matter whether the photobioreactor are immersed or float. The culture height in the tubes 63 is determined by the internal pressure in tubes 38.

The microorganisms of culture medium 1 have a permanent need for $CO_2$, hence the need to constantly charge the culture medium with dissolved $CO_2$. In order to ensure maximum $CO_2$ charging of the culture medium, according to the invention use is made of a carbonator 12 connected to the intake of each photobioreactor, as shown in FIG. 6.

This carbonator has a cylindrical inlet column 88, which is sealed at its two ends and which optionally contains a lining 90 such as Raschig rings or Bert supports. In said column 88, the culture medium arriving at the base of column 88, is charged with $CO_2$ introduced with the aid of a plunger tube 92, whose plunging end 94 is made from variable porosity fritted glass, in order to improve the $CO_2$ dissolving in liquid medium 1.

This inlet column 88 is connected to the upper part of an outlet column 96 into which is introduced the $CO_2$-charged liquid medium. Column 96 prevents the entrainment of $C_2$ and possibly support gas not dissolved in the culture medium to the associated photobioreactor. A pipe 98 for the discharge of undissolved $CO_2$ is provided at the top of the outlet column 96. As F3 indicated the flow direction of the liquid medium 1 in the carbonator.

The expansion tanks 2, like the other parts of the production apparatus, also help to prevent the deposition of microorganisms in the photobioreactor tubes 38 and consequently improve the efficiency of the said photobioreactors. To this end, use is advantageously made of tanks of the type shown in FIG. 7.

The shown tank has a parallelipipedic enclosure, whereof the lower end 102 is shaped like a funnel. This funnel or siloshaped tank has a widened bottom and permits the sedimentation and total recycling of the suspended organic matter (microorganisms plus products excreted by the microorganisms).

The tank has no sharp edge and the angles are rounded in order to prevent excessive fixing of the microorganisms and in order to facilitate the cleaning. It also has a diamond tip cover 104 in order to prevent the accumulation of condensation, the tip of the cover being directed towards the top of the tank. Cover 104 is fixed to enclosure 100 by metal clips 106 or butterfly screws. An O-ring 108 ensures the necessary sealing between the enclosure and the cover.

The enclosure 100 of the tank and its cover 104 are transparent to permit observation, but also to combat the contaminations of certain light-sensitive microorganisms. It is made from Plexiglass or PVC (polyvinylchloride).

In its upper part, a culture (microorganism) intake 110 permits a central filling of the hopper with microorganisms. In addition, supply pipes 112, 22, 114, and 116 are provided for the respective introduction into the tank 2 of the culture medium during the filling of the apparatus, the culture medium during continuous operation, the pH regulator (acid or basic) and the antifoaming agent.

A high level probe 118 and a low level probe 120 respectively make it possible to prevent an overflow or complete emptying of the tank 2 during continuous operation of the production apparatus.

In the upper part of the tank, a first planar metal grid 122 and a second metal grid 124 are provided. The first grid with a 1 cm mesh makes it possible, any use of self-cleaning polyurethane balls to recover the latter. The second grid of 1 mm mesh and in diamond point makes it possible to recover large cellular aggregates resulting from the selfcleaning by the balls. The tip of the grid is directed towards the bottom of the tank. Culture medium is discharged to the photobioreactors by pipe 126, a stop valve 128 being fitted thereto at the lower end 102 of the tank.

As has been stated hereinbefore, a regulation 19 of the $CO_2$ supply of the culture medium as a function of the solar radiation is provided. This regulation system 19 is shown in FIG. 8a. It comprises a pyranometer 130 supplying a voltage of 0 to 10 mV representing the light energy variations. This electric signal is amplified with the aid of a variable gain amplifier 132 between 0 and 5 V. The maximum amplification represents the flow rate of valve 134 when completely opened and which is mounted on pipe 18 (FIG. 1). A RC circuit 136 makes it possible to reduce the response of valve 134 to very short duration light variations.

The use of a variable gain amplifier 132 makes it possible to modify the sensitivity of system 19, i.e. the choice of the light intensity level determining the complete opening of valve 134. A regulation of the zero threshold S makes it possible to choose the solar energy threshold triggering the opening of valve 134. This adaptation makes it possible to take account of the compensation point of the photosynthesis microorganisms.

The amplified signal leaving circuit 136 is supplied to an electronic valve control circuit 138, valve 134 being an electronic valve of type 5850TR. The valve can be manually controlled by an external supply 140 (0–5 V) or automatically by means of a compute 142. A matching circuit 144 is located between the computer and the RC circuit.

As shown in FIG. 8b, this regulating system 19 makes it possible to supply the culture medium with $CO_2$ as a function of the variations of the light energy E during the time t expressed in minutes. Curve I represents the solar energy variations, curve II the variations in the $CO_2$ supply of the culture medium and curve III the unconsumed $CO_2$ variations.

The photosynthesis activity (fixing of the $CO_2$ by the microorganisms) is proportional to the light intensity. However, the intensity of the solar flux is variable during the day, being at a minimum morning and evening and at a maximum when the sun is at the zenith. Thus, a constant $CO_2$ supply leads to significant $CO_2$ losses morning and evening (low photosynthesis activity) and sometimes to a limitation of the photosynthesis by lack of $CO_2$ when the light intensity is at a maximum. Thus, the $CO_2$ regulation makes it possible to economize on $CO_2$, because its supply is proportional to the biological demand.

The production apparatus according to the invention can be used for the development and culture of plant cells or unicellular algae, such as those described in the publication by G. Gudin and C. Thepenier "Bioconversion of solar energy into organic chemicals by microalgae" published in Advances in Biotechnological Processes 6, pp 73–110, 1986.

The nutrient media of the latter contain various mineral salts, metallic salts, amino acids, vitamins and growth regulators. Examples of nutrient elements usable in the invention are illustrated by FR-A-2 324 224 and FR-A-2 361 060.

The production apparatus described hereinbefore permits an industrial production of approximately 60 tonnes per annum of biomass such as porphyridium cruentum, scenedesmus acutus, dunalulla on an industrial scale using tubular photobioreactors distributed over a water surface of 1 hectare, operating 300 days per annum and with an illumination period of on average 12 hours daily (which corresponds to a solar energy of 950 W/m$^2$), a fixed $CO_2$ quantity per annum of 56,000 m$^3$, i.e. 110 tonnes per annum and a daily nutrient medium quantity of 50 m$^3$, which corresponds to approximately 30 kg of urea per day, the oxygen quantity discharged into the atmosphere being 56,000 m$^3$ per annum, or 154 tonnes per annum.

What is claimed:

1. Apparatus for the intensive, controlled production by photosynthesis of microorganism suspended in a liquid medium comprising;

at least one photobioreactor (6) to be placed on an expanse of water (8) and having a first group of tubes (38), which are transparent to light and in which circulates the liquid medium (1), and a second group of tubes (62) disposed and maintained beneath the first group of tubes by means of regularly spaced, detachable interpolated members (70), said second group being able to make the photobioreactor submersible or non-submersible, control means (66,67,68) for the second group of tubes with a view to the immersion or non-immersion of the photobioreactor (6), at least one carbonator (12) connected to and inlet (10) of the photobioreactor in order to charge the liquid medium with the $CO_2$ necessary for photosynthesis, at least one degassing means (36) connected to the photobioreactor for eliminating from the liquid medium (1) oxygen produced by the microorganisms and possibly undissolved $CO_2$ and at least one expansion tank (2) connected to the photobioreactor (6) in order to reduce possible variations in the volume within the photobioreactor (6).

2. Production apparatus according to claim 1, characterized in that the interpolated members (70) are Y-shaped and the tails thereof are mounted on at least one rigid support (72) disposed between the first and second groups of tubes and which are interconnected with the aid of flexible connections (76) the tubes (38,62) of the first and second groups being placed between two Y's (70).

3. Production apparatus according to claim 1 or 2, characterized in that the tubes (38) of the first group are interconnected so as to form a coil, the ends of the tubes being provided with connections (44), to which is connected the degassing means (36).

4. Production apparatus according to any of the claims 1 to 3, characterized in that the tubes (62) of the second group are interconnected so as to form a coil.

5. Production apparatus according to claim 3, characterized in that the connections (44) are fixed to the tubes of the first group, each with the aid of a first (52a) and a second (52b) inner sleeves, mounted in respectively a first (38a) and a second (38b) tube of the first group, a first (54a) and a second (54b) outer sleeve in each of which are respectively located said first and second tubes.

6. Production apparatus according to claim 5, characterized in that the tubes (38) of the first group are made from polyethylene and the inner sleeves (52a,52b) and outer sleeves (54a,54b) are of polypropylene.

7. Production apparatus according to any one of the claims 1 to 6, characterized in that the interpolated members (70) are made from polypropylene.

8. Intensive, controlled production apparatus, by photosynthesis, of microorganisms suspended in a liquid medium comprising:

at least one photobioreactor (6) to be placed on an expanse of water (8) having a first group of light-transparent tubes (38), in which circulates the liquid medium, and a second group of tubes (62) placed beneath the first group, said second group being able to render the photobioreactor (6) submersible or non-submersible, means (66,67,68) for controlling the second group of tubes with a view to the immersion or non-immersion of the photobioreactor, at least one carbonator (12) connected to the intake (10) of the photobioreactor (6) for charging the liquid medium with the $C_2$ necessary for photosynthesis, said carbonator (12) having two columns including an intake column (88) in which the liquid medium (1) is charged with $CO_2$ and a discharge column (96), connected to the intake column into which is introduced the $CO_2$-charged liquid medium, at least one degassing means (36) connected to the photobioreactor (6) for eliminating from the liquid medium (1) in particular oxygen produced by the microorganisms, at least one expansion tank (2) connected to the photobioreactor (6) for reducing possible variations in the volume in the photobioreactor (6).

9. Production apparatus according to claim 8, characterized in that the intake column (88) has a plunger tube (92) for supplying $CO_2$ to the liquid medium (1), whose plunging end (94) is of variable porosity, fritted stainless steel or glass.

10. Production apparatus according to claims 8 or 9, characterized in that the intake column (88) is provided with a lining (90) for assisting the introduction of $CO_2$ into the liquid medium (1).

11. Apparatus for the intense, controlled production by photosynthesis of microorganisms suspended in a liquid medium comprising:

at least one photobioreactor (6) to be placed on an expanse of water (8) having a first group of light-transparent tubes (38), in which circulates the liquid medium (1) and a second group of tubes (62) positioned beneath the first group, said second group being able to make the photobioreactor (6) submersible or non-submersible, means (67,66,68) for controlling the second group of tubes (62) with a view to the immersion or non-immersion of the photobioreactors, at least one carbonator (12) connected to the intake (10) of the photobioreactor for charging the liquid medium (1) with $C_2$ necessary for photosynthesis, at least one degassing means (36) connected to the photobioreactor (6) for eliminating from the liquid medium (1) in particular oxygen produced by the microorganisms, said degassing means (36) having a sealed external enclosure (78) with a longitudinal axis (79), a U-shaped duct (82) for collecting oxygen, whereof a branch (84) of said U-shaped duct is located in said enclosure (78) parallel to said axis and whereof a base (86) of said U-shaped duct is located on the side of the enclosure base (80), an end (85) of said duct (82) collecting oxygen issuing into the upper part of the enclosure, whereby at least one supply pipe (61) and at least one discharge pipe (63) for the liquid medium (1) is connected to the lower part of the enclosure, at least one expansion tank (2) connected to the photobioreactor (6) for reducing possible variations of the volume in the photobioreactor (6).

12. Production apparatus according any one of the claims 1 to 11, characterized in that the control means (66,67,68) of the second group of tubes (38) are of the pneumatic type and are used for inflating and deflating the tubes (62) of the second group respectively when the temperature of the liquid medium (1) is below a first reference temperature and when it is above a second reference temperature, the first reference temperature being below the second reference temperature.

13. Production apparatus according to any one of the claims 1 to 12, characterized in that the expansion tank (2) is transparent and formed from enclosure (100) with rounded edges, whereof the upper end is sealed by a diamond tip cover (104) and whose lower end is shaped like a funnel (102).

14. Production apparatus according to claim 13, characterized in that the tank is equipped in its upper part with a diamond tip metal grid (124).

15. Production apparatus according to any one of the claims 1 to 14, including means (19) for regulating the quantity of $C_2$ introduced into the photobioreactor (6) as a function of the solar energy.

* * * * *

UNITED STATES PATENT AND TRADEMARK OFFICE
CERTIFICATE OF CORRECTION

PATENT NO. : 4,868,123

DATED : September 19, 1989

INVENTOR(S) : Berson et al.

It is certified that error appears in the above-identified patent and that said Letters Patent is hereby corrected as shown below:

Column 1, line 30, delete "of" (second occurrence) and insert --or--.

Column 2, line 38, delete "control" and insert --controlled--.

Column 6, line 15, delete "he" and insert --the--.

Column 7, line 50, after "immersion" insert --,--.

Column 8, line 14, after "Y's" insert --,--.

Column 10, line 10, delete "photosynthesis" and insert --photosynthetic--.

Column 10, line 15, delete "compute" and insert --computer--.

Column 10, line 25, delete "photosynthesis" and insert --photosynthetic--.

Column 10, line 31, delete "photosynthesis" and insert --photosynthetic--.

Column 11, line 11, delete "and" and insert --an--.

Column 12, line 1, delete "$C_2$" and insert --$CO_2$--.

Column 12, line 36, delete "photobioreactors" and insert --photobioreactor--.

Column 12, line 39, delete "$C_2$" and insert --$CO_2$--.

Column 13, line 1, after "from" insert --an--.

UNITED STATES PATENT AND TRADEMARK OFFICE
CERTIFICATE OF CORRECTION

PATENT NO. : 4,868,123

DATED : September 19, 1989

INVENTOR(S) : Berson, et al

It is certified that error appears in the above-identified patent and that said Letters Patent is hereby corrected as shown below:

Column 14, line 5, delete "$C_2$" and insert --$CO_2$--.

Signed and Sealed this

Twenty-eighth Day of August, 1990

Attest:

HARRY F. MANBECK, JR.

Attesting Officer

Commissioner of Patents and Trademarks